US00PP24557P2

(12) United States Plant Patent
Bergman

(10) Patent No.: US PP24,557 P2
(45) Date of Patent: Jun. 17, 2014

(54) ***CHRYSANTHEMUM* PLANT NAMED 'CIDZ0043'**

(50) Latin Name: *Chrysanthemum×morifolium*
Varietal Denomination: CIDZ0043

(71) Applicant: Syngenta Crop Protection AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 2 days.

(21) Appl. No.: 13/694,886

(22) Filed: Jan. 15, 2013

(51) Int. Cl.
*A01H 5/00* (2006.01)

(52) U.S. Cl.
USPC ..... Plt./286

(58) Field of Classification Search
USPC ..... Plt./286, 295, 297
See application file for complete search history.

*Primary Examiner* — Anne Grunberg
(74) *Attorney, Agent, or Firm* — Joshua L. Price

(57) ABSTRACT

A new *Chrysanthemum* plant named 'CIDZ0043' particularly distinguished by the light red-purple and yellow basal banded ray florets on daisy form inflorescences, with medium green foliage on strong and sturdy plants.

1 Drawing Sheet

Latin name of the genus and species of the plant claimed: *Chrysanthemum×morifolium.*

Varietal denomination: 'CIDZ0043'.

BACKGROUND OF THE NEW PLANT

The present invention comprises a new *Chrysanthemum*, botanically known as *Chrysanthemum×morifolium*, and hereinafter referred to by the variety name 'CIDZ0043'.

'CIDZ0043' is a product of a planned breeding program. The new cultivar has light red-purple and yellow basal banded ray florets on daisy form inflorescences with medium green foliage on strong and sturdy plants.

'CIDZ0043' originates as a whole plant mutation of 'CIDZ0006', U.S. Plant Pat. No. 22,955. 'CIDZ0043' was discovered and selected by the inventor as a single flowering plant within a large population of the parent cultivar, grown outdoors in a saran field structure in Fort Myers, Fla. in November 2009. The parent cultivar 'CIDZ0006' has red-purple ray florets with a green and yellow basal spot.

The first act of asexual reproduction of 'CIDZ0043' was accomplished when vegetative cuttings were propagated from the initial selection in January 2010 in a greenhouse in Fort Myers, Fla.

BRIEF SUMMARY OF INVENTION

Horticultural examination of plants grown from cuttings of the plant initiated in February 2010, and continuing thereafter, has demonstrated that the combination of characteristics as herein disclosed for 'CIDZ0043' are firmly fixed and are retained through successive generations of asexual reproduction.

'CIDZ0043' has not been observed under all possible environmental conditions. The phenotype may vary significantly with variations in environment such as temperature, light intensity, and day length.

A Plant Breeder's Right for this cultivar was applied for in Canada on Jun. 29, 2012 (12-7647). 'CIDZ0043' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIDZ0043' with colors being as true as possible with an illustration of this type.

Figure 1:
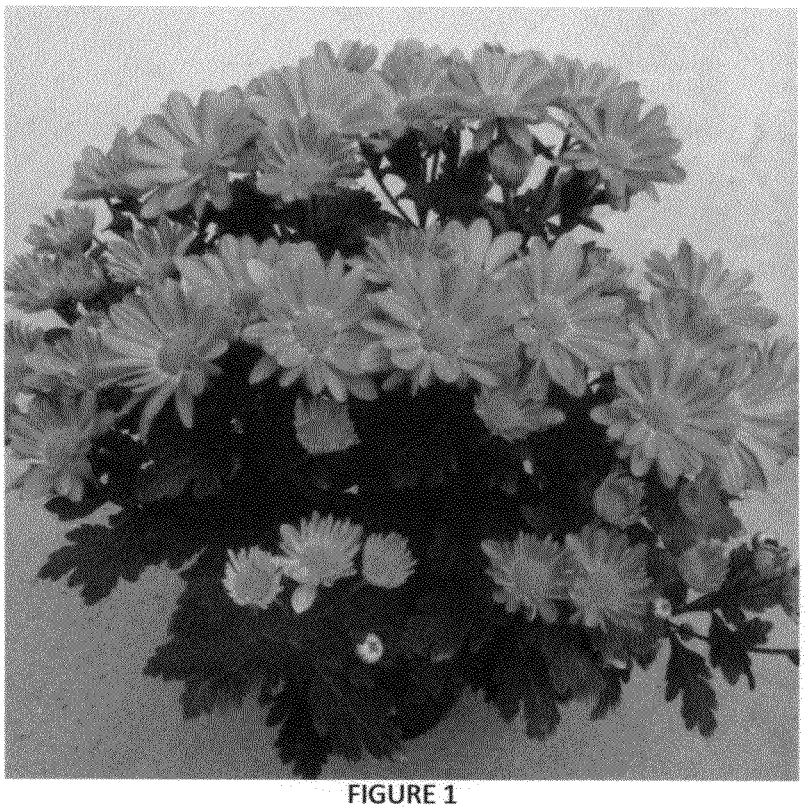
Figure 2:
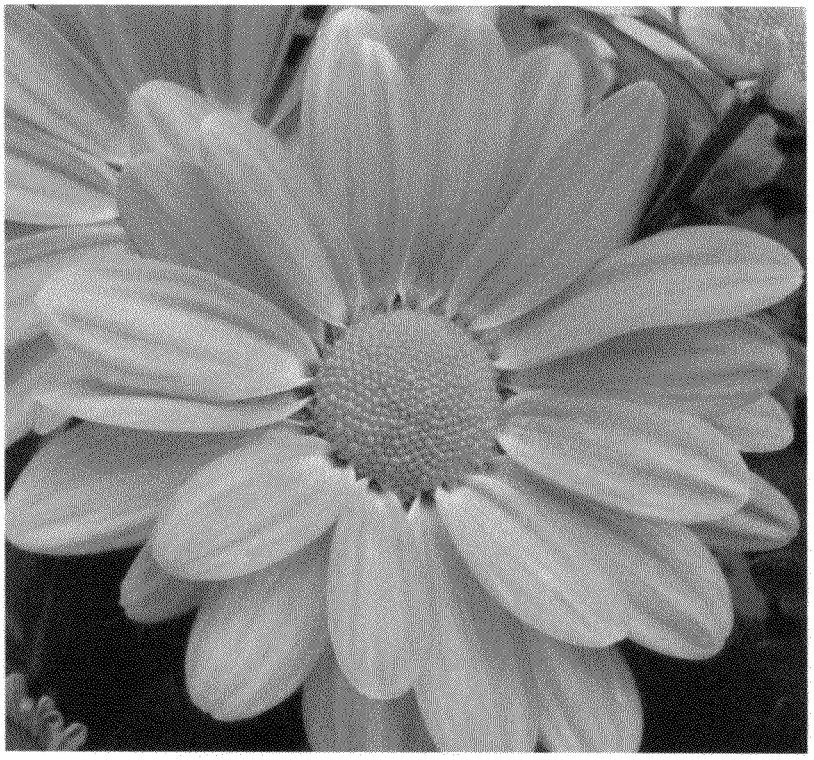

The photographic drawing shows in FIG. 1, 4 flowering plants of the new variety growing in 1 container, and in FIG. 2, a close-up of the inflorescences.

DETAILED BOTANICAL DESCRIPTION

The plant descriptions, measurements and aforementioned photographs were taken in Gilroy, Calif. in early October 2012 under natural light. These plants were grown 4 plants in a 6 inch container in a greenhouse in Nipomo, Calif. These plants used in the photograph and descriptions were about 10-12 weeks old.

Color references are made to The Royal Horticultural Society Colour Chart (R.H.S.) 2001.

TABLE 1

DIFFERENCES BETWEEN THE NEW VARIETY 'CIDZ0043' AND A MOST SIMILAR VARIETY (COLOR)

| | 'CIDZ0043' | 'Yoeugene' (U.S. Plant Pat. No. 11,917) |
|---|---|---|
| Ray floret color: | Medium red-purple with a yellow basal blotch | Somewhat darker red-purple |

TABLE 1-continued

DIFFERENCES BETWEEN THE NEW VARIETY 'CIDZ0043' AND A MOST SIMILAR VARIETY (COLOR)

| | 'CIDZ0043' | 'Yoeugene' (U.S. Plant Pat. No. 11,917) |
|---|---|---|
| Ray floret petal shape: | Flatter | Can show some rolling of petal sides |
| Flowering response: | 3-4 days slower | 3-4 days faster |
| Plant habit: | More vigorous/taller | Less vigorous/shorter |

TABLE 2

DIFFERENCES BETWEEN THE NEW VARIETY 'CIDZ0043' AND A MOST SIMILAR VARIETY (PLANT HABIT)

| | 'CIDZ0043' | 'CIDZ0006' (U.S. Plant Pat. No. 22,955) |
|---|---|---|
| Ray floret color: | Brighter more intense red-purple with brighter yellow blotch | Less intense red-purple with yellow and green basal blotch |
| Foliage size: | Larger | Smaller |
| Peduncle length: | Somewhat shorter | Somewhat longer |
| Inflorescence diameter: | Smaller | Larger |

Plant:

*Form, growth and habit*.—Herbaceous pot-type, stems upright, strong and study growth habit.

*Plant height*.—25-27.0 cm.

*Plant height* (*inflorescence included*).—28-32.0 cm.

*Plant width*.—17-21.0 cm.

Roots:

*Number of days to initiate roots*.—About 4 days at about 22 degrees C.

*Number of days to produce a rooted cutting*.—4-6 days at 22 degrees C.

*Type*.—Fine, fibrous, free branching.

*Color*.—RHS N155B but whiter.

Foliage:

*Arrangement*.—Alternate.

*Immature, leaf color, upper surface*.—Closest to but darker than RHS 137A.

*Immature, leaf color, lower surface*.—RHS 137C.

*Mature, leaf color, upper surface*.—RHS 137A to RHS 137B.

*Mature, leaf color, lower surface*.—RHS 137C to RHS 137D.

*Length*.—6.4-6.9 cm.

*Width*.—4-4.7 cm.

*Shape*.—Ovate.

*Base shape*.—Attenuate.

*Apex shape*.—Mucronulate.

*Margin*.—Irregularly and slightly incised, slightly dentate.

*Texture, upper surface*.—Bifid T-shaped hairs.

*Texture, lower surface*.—Bifid T-shaped hairs.

*Color of veins, upper surface*.—RHS 144B.

*Color of veins, lower surface*.—RHS 144B.

*Pattern of veining*.—Palmate.

*Petiole color*.—RHS 144B.

*Length*.—1.5-2.0 cm.

*Diameter*.—0.3-0.4 cm.

*Texture*.—Bifid T-shaped hairs.

Stem:

*Quantity of main branches per plant*.—3-5.

*Color of stem*.—Closest to RHS 138A but appears lighter due to hairs.

*Length of stem*.—20-24.0 cm.

*Diameter*.—0.4-0.5 cm.

*Length of internodes*.—0.5-1.0 cm.

*Texture*.—Bifid T-shaped hairs.

*Color of peduncle*.—Closest to RHS 138A but appears lighter due to hairs.

*Length of peduncle*.—8-9.0 cm.

*Peduncle diameter*.—0.2-0.25 cm.

*Texture*.—Bifid T-shaped hairs.

Inflorescence:

*Type*.—Compositae, solitary inflorescences borne terminally above foliage, ray florets arranged acropetally on a capitulum.

*Quantity of short days to flowering* (*response time*).—About 58 days.

*Natural season flowering*.—Not determined to date.

*Quantity of inflorescences per plant*.—13-19 with 2-8 buds.

*Lastingness of individual blooms on the plant*.—About 4 weeks.

*Fragrance*.—Slightly spicy.

Bud (just when opening/showing color):

*Color*.—RHS 3C quickly becoming RHS 5C with increasing hints of red-purple.

*Length*.—1.3-1.6 cm.

*Width*.—1.5 cm.

*Shape*.—Oblate.

Immature inflorescence:

*Diameter*.—2.7-3.1 cm naturally; About 4.5 cm when flattened out.

*Color of ray florets, upper surface*.—RHS 5B to RHS 5C, lightly and somewhat irregularly overlaid with hues of RHS N66D to RHS N66B and a RHS 5B basal blotch.

*Color of ray florets, lower surface*.—About RHS 10C with only hints of the upper surface color showing through.

Mature inflorescence:

*Diameter*.—6.8-7.1 cm.

*Depth*.—2.0 cm.

*Total diameter of disc*.—1.7-1.8 cm.

*Receptacle color*.—RHS 145C.

*Receptacle height*.—0.5 cm.

*Receptacle diameter*.—0.8 cm.

Ray florets:

*Average quantity of florets*.—23-28 in 2-3 whorls.

*Color of florets, upper surface*.—RHS 4C overlaid with RHS N57D mainly on the lower half, to RHS N66C mainly on the outer half towards apex, with a RHS 5B basal blotch.

*Color of florets, lower surface*.—About RHS 10C with only hints of the upper surface color showing through.

*Length*.—2.9-3.4 cm.

*Width*.—1.1 cm.

*Shape*.—Broadly elliptical.

*Apex shape*.—Emarginate.

*Base shape*.—Cuneate.

*Margin*.—Entire.

*Texture, upper surface*.—Papillose.

*Texture, lower surface*.—Papillose.

Disc florets:

*Average quantity of florets*.—About 400.

*Color of florets*.—RHS 4C with a RHS 13C apex and on the very immature a spot of RHS 145A on the very top.

*Length*.—0.5 cm.

*Width*.—0.1 cm.

*Shape*.—Tubular, elongated.

*Apex shape*.—Acute, 5 pointed.

*Texture, inner surface*.—Glabrous.

*Texture, outer surface*.—Glabrous.

Phyllaries:

*Quantity*.—25-29.

*Color, upper surface*.—RHS 137B.

*Color, lower surface*.—RHS 137B but appears lighter due to hairs.

*Length*.—0.6-0.9 cm.

*Width*.—0.15 cm.

*Shape*.—Lanceolate.

*Apex shape*.—Acute.

*Base*.—Fused.

*Margins*.—Entire; some with papery edges.

*Texture, upper surface*.—Glabrous.

*Texture, lower surface*.—Bifid T-shaped hairs.

Reproductive organs:

*Pistil*.—1, found on both types of florets.

*Length*.—0.5-0.6 cm.

*Style color*.—RHS 1B.

*Style length*.—0.45-0.55 cm.

*Stigma color*.—RHS 13A.

*Stigma shape*.—Bi-parted; slightly fuzzy.

*Ovary*.—Not really developed to date.

*Stamens*.—4, found on only on the disc florets.

*Color of filaments*.—RHS 1C.

*Length filaments*.—0.2 cm.

*Anther color*.—RHS 13C.

*Anther length*.—0.2 cm.

*Anther shape*.—Oblong.

*Pollen*.—Not really developed and dehisced to date.

*Fertility/seed set*.—Has not been observed to date.

*Disease/pest resistance*.—Has not been observed to date.

What is claimed is:

1. A new and distinct variety of *Chrysanthemum* plant named 'CIDZ0043' substantially as illustrated and described herein.

* * * * *